US008728289B2

(12) United States Patent
Dinsmoor et al.

(10) Patent No.: US 8,728,289 B2
(45) Date of Patent: May 20, 2014

(54) MONOLITHIC ELECTRODES AND PH TRANSDUCERS

(75) Inventors: David A. Dinsmoor, St. Paul, MN (US); Michael F. Mattes, Chandler, AZ (US); Rogier Receveur, Maastricht (NL); Arun K. Gupta, Hermantown, MN (US)

(73) Assignee: Medtronic, Inc., Minneapolis, MN (US)

( * ) Notice: Subject to any disclaimer, the term of this patent is extended or adjusted under 35 U.S.C. 154(b) by 1806 days.

(21) Appl. No.: 11/304,065

(22) Filed: Dec. 15, 2005

(65) Prior Publication Data

US 2007/0138027 A1    Jun. 21, 2007

(51) Int. Cl.
*G01N 27/333*    (2006.01)

(52) U.S. Cl.
USPC ........ 204/416; 204/417; 204/419; 205/787.5; 205/775; 205/789; 205/792; 205/793

(58) Field of Classification Search
USPC ................. 204/433, 420, 416, 400, 419, 428; 205/787.5, 775, 782.5, 789, 793
See application file for complete search history.

(56) References Cited

U.S. PATENT DOCUMENTS

| | | | |
|---|---|---|---|
| 4,592,824 A | | 6/1986 | Smith et al. |
| 4,748,562 A | | 5/1988 | Miller et al. |
| 4,786,396 A | * | 11/1988 | Yee et al. .................. 204/420 |
| 4,814,058 A | * | 3/1989 | Bordenick .................. 204/401 |
| 4,857,166 A | * | 8/1989 | Kotani ........................ 204/435 |
| 4,874,500 A | * | 10/1989 | Madou et al. .............. 204/412 |
| 4,975,175 A | * | 12/1990 | Karube et al. .......... 204/403.12 |
| 5,660,741 A | | 8/1997 | Suzuki et al. |
| 5,814,280 A | | 9/1998 | Tomita et al. |
| 5,837,113 A | * | 11/1998 | Suzuki et al. ............... 204/420 |
| 6,689,056 B1 | | 2/2004 | Kilcoyne et al. |
| 6,896,793 B2 | | 5/2005 | Erdosy et al. |
| 6,897,081 B2 | | 5/2005 | Hsiung et al. |
| 2002/0121439 A1 | * | 9/2002 | Crumly et al. .............. 204/416 |
| 2003/0029722 A1 | | 2/2003 | Erdosy et al. |
| 2004/0018717 A1 | * | 1/2004 | Fornof et al. ............... 438/624 |

FOREIGN PATENT DOCUMENTS

EP    1 193 495 A2    4/2002

OTHER PUBLICATIONS

Altug, I.; et al. The Ion-Selective Prooerties of Sintered Porous Glass Membranes, J. Phys Chem. 1968, vol. 72, No. 8, pp. 2976-2981.*
Notification of Transmittal of the International Preliminary Report on Patentability dated Mar. 7, 2008 for corresponding application PCT/US2006/044956 (17 pgs.).
Notification of Transmittal of the International Search Report and the Written Opinion of the International Search Authority, or the Declaration dated Mar. 23, 2007 for corresponding application PCT/US2006/044956, filed Nov. 21, 2006 (13 pgs.).

(Continued)

*Primary Examiner* — Luan Van
*Assistant Examiner* — Gurpreet Kaur
(74) *Attorney, Agent, or Firm* — Shumaker & Sieffert, P.A.

(57) ABSTRACT

The disclosure provides monolithic electrodes including a substrate defining a walled cavity having a floor, an electrically conductive cathode layer overlaying the cavity floor, an electrically conductive contact pad overlaying the substrate, an electrically conductive via in electrical communication with the cathode layer and the contact pad, and a porous membrane layer overlaying the cavity and defining a chamber formed by the porous membrane layer, the walled cavity, and the cavity floor. The disclosure also provides pH transducers including monolithic indicator and reference electrodes, and methods of making and using monolithic pH electrodes and transducers.

39 Claims, 5 Drawing Sheets

(56) References Cited

OTHER PUBLICATIONS

Ion Selective Electrode, Oct. 31, 2005. http://en.wikipedia.org/wiki/Ion_selective_electrode, 3 pgs., Oct. 31, 2005.
Silver Chloride Electrode, http://en.wikipedia.org/wiki/Silver_Chloride_Electrode, 2 pgs., Oct. 31, 2005
Standard Hydrogen Electrode, http://en.wikipedia.org/wiki/Hydrogen_electrode, 2 pgs., Oct. 31, 2005.
Electrode Basics, http://www.omega.com/techref/ph-3.html, 2 pgs., Oct. 31, 2005.
The Combination pH Electrode, http://www.chem.usu.edu/~sbialkow/Classes/3600/Overheads/pH/ionselective.html, 5 pgs., Oct. 31, 2005.
Glass electrode, http://en.wikipedia.org/wiki/PH_glass_electrode, 3 pgs., Oct. 31, 2005.
R. Stuart Mackay: Bio-Medical Telemetry, Sensing and Transmitting Biological Information from Animals and Man, 2d ed., IEEE Press New York, 1993 entitled: Electronics: Power Sources, pp. 62-70.
Jochen Kuhmann, "Very Small Form Factor Silicon Package Enables Low Cost Wafer-Level Assembly and Surface Mount Technology (SMT), Hymite," The MEMS Packing Revolution, 20 pgs. Meptec, 2005.

* cited by examiner

MONOLITHIC ELECTRODES AND PH TRANSDUCERS

TECHNICAL FIELD

The invention relates to sensing electrodes, and more particularly to electrodes useful in transducers for measurement of pH.

BACKGROUND

Gastroesophageal reflux is a condition in which gastric acid refluxes, or flows in the direction opposite to the normal flow, from the stomach into the esophagus. Frequent reflux episodes may result in a potentially severe problem known as gastroesophageal reflux disease (GERD). GERD is the most common cause of dyspepsia or heartburn. GERD affects approximately 75 million adults in the United States on at least an intermittent basis, and approximately 13 million adults on a daily basis. As a common cause of chest pain, GERD frequently mimics the symptoms of a myocardial infarction or severe angina pectoris, which are signs of severe coronary artery disease. Because their treatments and outcomes are different, distinguishing between GERD and coronary artery disease is of paramount diagnostic importance to the patient and physician. Complications of GERD may include esophageal erosion, esophageal ulcer, and esophageal stricture. Prolonged exposure of esophageal mucosa to acid often leads to a precancerous condition known as Barrett's esophagus.

Efforts have been made to define and report as reflux rapid changes of intraesophageal pH, even while the pH remains within the normal esophageal pH range of 4 to 7. Such pH changes, however, can be difficult to prove to be caused by true gastroesophageal reflux, and in some instances may not be caused by reflux. The primary and most reliable method of objectively diagnosing GERD is 24-hour measurement of pH within the lower esophagus. A pH reading corresponds to the negative logarithm of the hydrogen ion concentration, and is represented on a scale of 0 to 14, with pH values above 7 corresponding to basic conditions, and pH values below 7 corresponding to acidic conditions. As a general rule, when gastric acid enters the esophagus from the stomach, the intraesophageal pH drops below 4. An epoch of one second or more during which the intraesophageal pH falls below 4 is generally considered a reflux event.

Sensing electrodes have been used to measure pH. Electrodes are generally of three types, counter electrodes, indicator electrodes and reference electrodes. A counter electrode acts as a sink for a current path. An indicator electrode (also known as a working or measurement electrode) selectively measures a specific chemical species, such as an ion. A reference electrode generally serves as an electrical reference point in an electrochemical device against which electrical potentials are measured and controlled. When electrical potentials are measured by an indicator electrode, the method is termed potentiometry.

SUMMARY

In general, the disclosure relates to sensing electrodes, particularly monolithic electrodes useful in transducers for potentiometric measurement of pH. In some aspects, transducers incorporating monolithic reference electrodes may be useful for measuring intraesophageal pH.

In one embodiment, the disclosure provides a monolithic electrode including a substrate defining a walled cavity having a floor, an electrically conductive cathode layer overlaying the cavity floor, an electrically conductive contact pad overlaying the substrate, an electrically conductive via in electrical communication with the cathode layer and the contact pad, and a porous membrane layer overlaying the cavity and defining a chamber formed by the porous membrane layer, the walled cavity, and the cavity floor. In certain embodiments useful as pH reference or indicator electrodes, the cathode layer may include a silver chloride layer overlaying a silver layer.

In another embodiment, the disclosure provides a transducer including a substrate, an indicator electrode formed on the substrate, and a reference electrode formed on the substrate and electrically connected to the indicator electrode. In certain presently preferred embodiments, one or both of the indicator electrode and the reference electrode include a walled cavity having a floor defined by the substrate, a silver layer overlaying the cavity floor, a silver chloride layer overlaying the silver layer, an electrically conductive contact pad overlaying the substrate, an electrically conductive via in electrical communication with the silver layer and the contact pad, and a porous membrane layer overlaying the cavity and defining a chamber formed by the porous membrane layer, the walled cavity, and the cavity floor.

In another embodiment, the disclosure provides a method for fabricating a monolithic electrode, including forming a walled cavity in a surface of a substrate wherein the cavity has a floor defined by the substrate, depositing an insulative layer overlaying a substrate and defining a walled cavity, wherein the insulative layer forms a cavity floor, depositing a silver layer overlaying the cavity floor, depositing a silver chloride layer overlaying the silver layer, depositing an electrically conductive contact pad overlaying the substrate, forming an electrically conductive via in electrical communication with the silver layer and the contact pad, and applying a porous membrane layer overlaying the cavity, thereby defining a chamber formed by the porous membrane layer, the walled cavity, and the cavity floor.

In yet another embodiment, the disclosure provides a method for sensing pH within a body lumen, including inserting into the body lumen a monolithic pH transducer including a substrate, a pH indicator electrode formed on the substrate, a pH reference electrode formed on the substrate and electrically connected to the indicator electrode through a high impedance pH monitor formed on the substrate; attaching the pH transducer to the inner wall of the body lumen; and recording the pH within the body lumen as measured by the pH monitor and pH transducer. In certain embodiments, the method may be used to measure intraesophageal pH.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
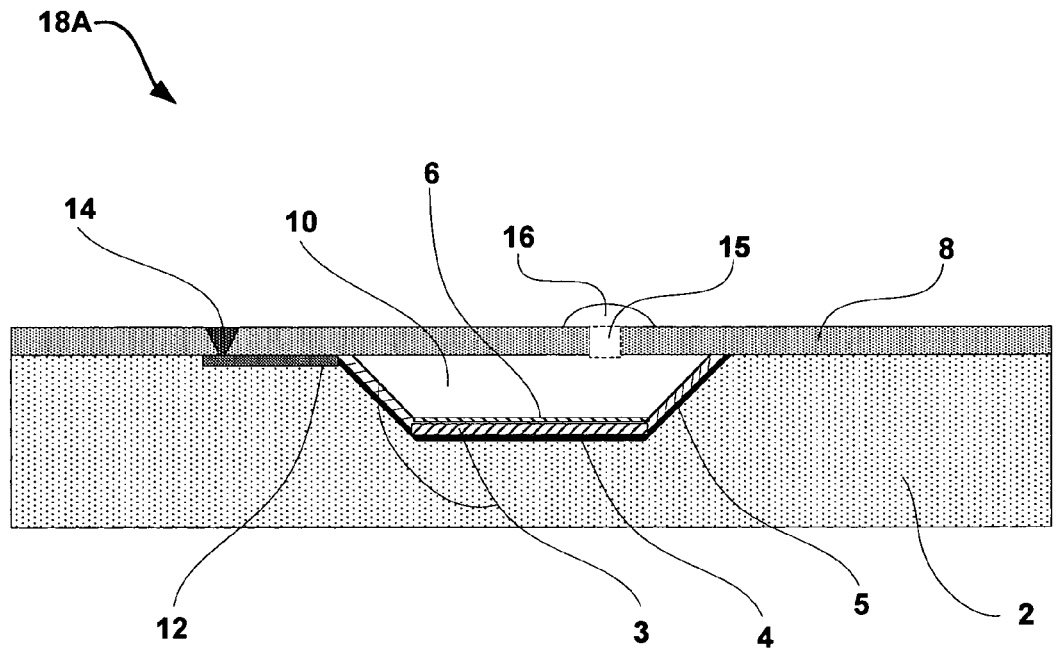
FIG. 1 is a cross-sectional side view diagram illustrating a reference electrode according to one embodiment of the invention.

The invention provides monolithic electrodes useful as transducers for measurement of physiochemical parameters such as pH, of fluid samples such as body fluids, including, but not limited to, measurement of intraesophageal pH for detection of gastroesophageal reflux. The monolithic electrodes may also be useful in durable transducers for measuring physiological parameters such as the unbound concentration or activity of blood gases (such as, e.g., oxygen and carbon dioxide), ion concentration in body fluids (such as, e.g., sodium, chloride, potassium, magnesium, lithium, ammonium and calcium), blood pH and hematocrit. Alternative embodiments of the invention may be adapted to measure physiochemical parameters such as glucose, lactate or other enzymes or blood solutes.

As used herein, the term "electrode" generally refers to a component of an electrochemical device that makes the interface between an external ionic medium and the internal electrical conductor. The external ionic medium is typically an aqueous solution with dissolved salts.

A "sensing electrode" as used herein generally refers to the electrically connected combination of a "reference electrode", containing a known ionic concentration electrolyte, and an "indicator electrode," which exchanges ions in response to exposure of the indicator electrode to a sample or calibration fluid.

As used herein, the term "electrochemical sensor" may generally comprise a device that includes a sensing electrode that responds to variations in the concentration of a given chemical species in a sample, such as a body fluid sample. For pH measurements, an electrochemical sensor responsive to variations in hydrogen ion concentration is generally used, typically with electrically connected indicator and reference electrodes containing silver and silver chloride and an electrolyte solution of potassium chloride.

The term "monolithic pH transducer" generally includes one or more pH "sensing electrodes" combined on a single substrate and optionally including a pH monitor, a transmitter, a microprocessor (CPU) and a power supply.

As used herein, the term "liquid junction" generally refers to the interface between the electrolyte solution and a sample or calibrating solution.

The term "sample" as used herein generally refers to any fluid or solution analyte which may be tested using the sensing electrode, including, for example, an aqueous solution, such as a reference or calibrating solution, or a body fluid, such as gastric acid, bile, mucous, blood, plasma, synovial fluid, and urine.

As used herein, the term "calibration" generally refers to the process by which the response characteristics of a sensor to a specific analyte are determined quantitatively. To calibrate a sensor, the sensor is exposed to at least two reagent samples or calibrating solutions, each reagent sample having a different, known concentration of an analyte. The responses (i.e., signals) measured by the sensor, relative to the concentrations of the analyte in the two different reagent samples, may serve as reference points for measurements of the analyte in samples having unknown concentrations of the analyte.

The "substrate" as used herein generally refers to the support for a sensing electrode upon which the various layers (such as, e.g., silver (Ag), silver chloride (AgCl), insulating layers, contacts pads, glazes, and the like) of the sensing electrode are applied, formed, or deposited.

A "via" is generally an electrically conductive element in electrical communication with at least two additional electrically conductive elements of an electrical circuit, for example, between an electrically conductive pad and an electrically conductive silver layer in an electrode.

A "porous membrane" as used herein generally refers to the layer that overlays the cavity and allows the passage, or transfer, of the ion(s) of interest.

A "reference solution" as used herein generally refers to an aqueous liquid or a gel containing a known ionic concentration of NaCl, KCl, or the like.

In general, the invention provides a monolithic electrode including a substrate defining a walled cavity having a floor, an electrically conductive cathode layer overlaying the cavity floor, an electrically conductive contact pad overlaying the substrate, an electrically conductive via in electrical communication with the cathode layer and the contact pad, and a porous membrane layer overlaying the cavity and defining a chamber formed by the porous membrane layer, the walled cavity, the cavity floor, and a reference solution contained in said cavity. In certain embodiments useful as pH reference or indicator electrodes, the cathode layer may include a silver chloride layer overlaying a silver layer.

The following examples and figures describe exemplary embodiments of monolithic pH electrodes and transducers in which the electrically conductive cathode layer is selected to include silver overlayed with silver chloride. However, one skilled in the art will understand that the invention extends to other types of sensing electrodes, for example, ion specific electrodes, gas sensing electrodes, and the like. Thus in the following exemplary embodiments, the silver layer and overlaying silver chloride layer illustrate one exemplary electrically conductive cathode layer. However, virtually any electrically conductive material, for example one or more metals selected from silver, gold, platinum, palladium, rhenium and mercury, may be substituted for the silver/silver chloride layers in the examples without departing from the scope of the disclosed embodiments.

In one embodiment illustrated in FIG. 1, the invention provides an electrode 18A including a substrate 2 defining a floor 4 of a walled cavity 5 having walls defined by an electrically conductive material deposited on the substrate 2, a silver layer 3 overlaying at least a portion of the cavity floor 4, a silver chloride layer 6 overlaying at least a portion of the silver layer 3, an electrically conductive contact pad 12 overlaying at least a portion of the substrate 2, an electrically conductive via 14 in electrical communication with the silver layer 3 and the contact pad 12; and a porous membrane layer 8 overlaying the cavity 5 and defining a chamber 10 formed by the porous membrane layer 8, the walled cavity 5, and the cavity floor 4. In this embodiment, the via 14 communicably extends through a top and bottom surface of the porous membrane layer 8 to the contact pad 12, which is electrically connected to the silver layer 3.

Figure 2:
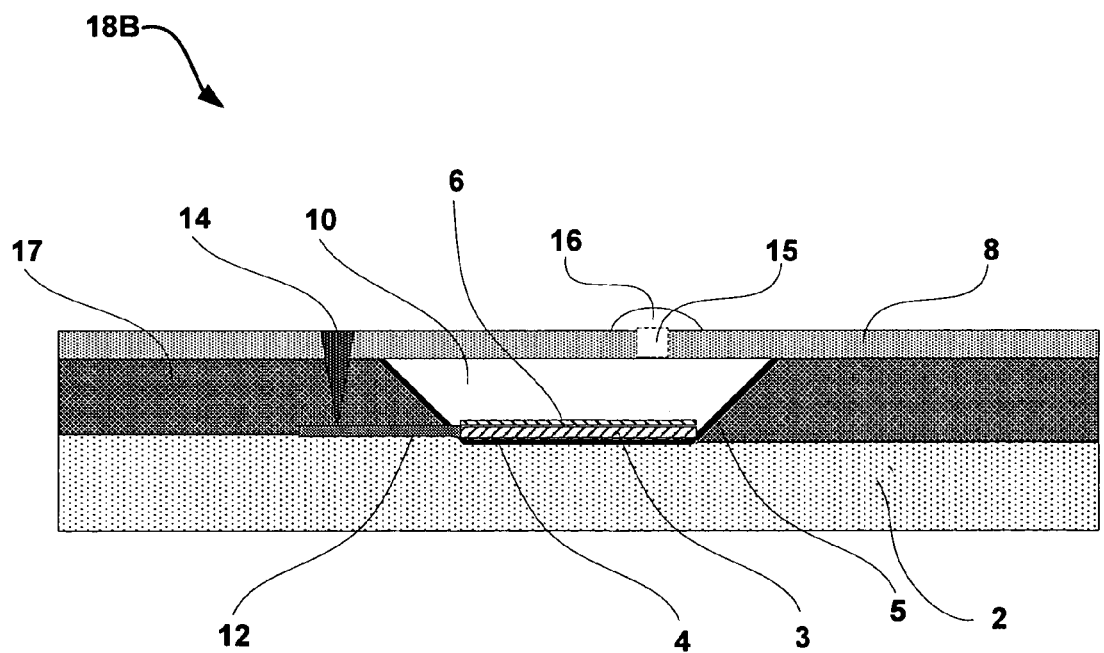
FIG. 2 is a cross-sectional side view diagram illustrating a reference electrode according to another embodiment of the invention.

In another embodiment illustrated in FIG. 2, the invention provides an electrode 18B including a substrate 2 defining a floor 4 of a walled cavity 5 wherein the walls of the cavity are formed by an insulative layer 17 overlaying the substrate 2, a silver layer 3 overlaying at least a portion of the cavity floor 4, a silver chloride layer 6 overlaying at least a portion of the silver layer 3, an electrically conductive contact pad 12 positioned between the insulative layer 17 and the substrate 2 and overlaying at least a portion of the substrate 2, an electrically conductive via 14 in electrical communication with the silver layer 3 and the contact pad 12, and a porous membrane layer 8 overlaying the cavity 5 and defining a chamber 10 formed by the porous membrane layer 8, the walled cavity 5, and the cavity floor 4. In the embodiment of FIG. 2, the via 14 communicably extends through a top and bottom surface of the porous membrane layer 8 and through the insulative layer 17 to the contact pad 12, which is electrically connected to the silver layer 3.

Figure 3:
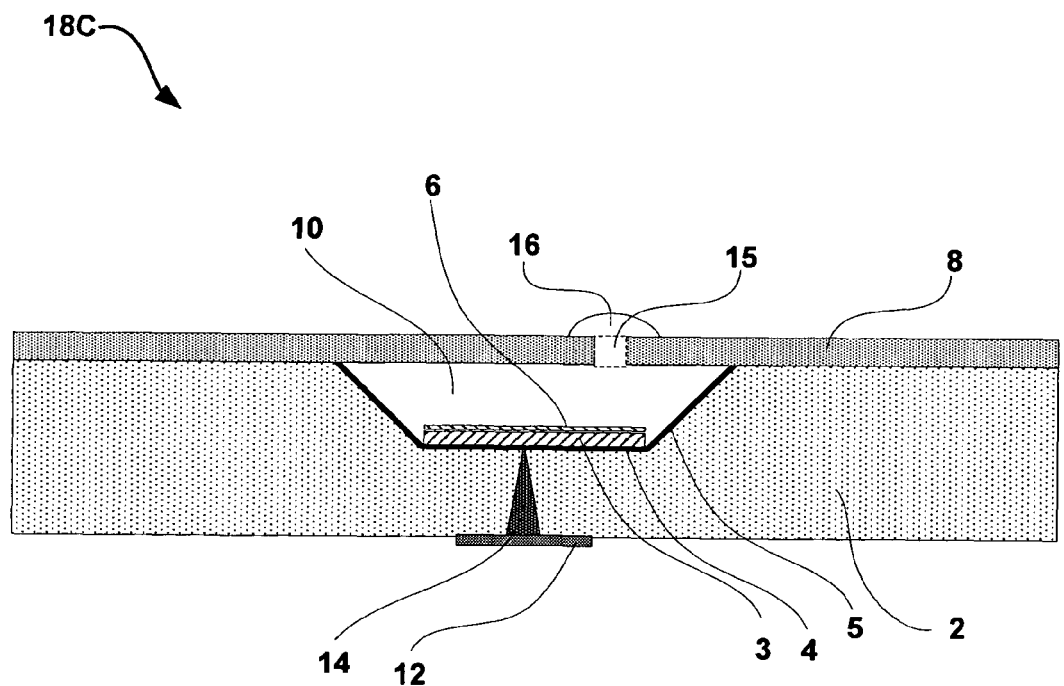
FIG. 3 is a cross-sectional side view diagram illustrating a reference electrode according to an alternative embodiment of the invention.

In yet another embodiment illustrated in FIG. 3, the invention provides an electrode 18C including a substrate 2 defining a floor 4 of a walled cavity 5, a silver layer 3 overlaying at least a portion of the cavity floor 4, a silver chloride layer 6 overlaying at least a portion of the silver layer 3, an electrically conductive contact pad 12 positioned on an outer surface of the substrate 2 and overlaying at least a portion of the substrate 2 at a lower surface of the substrate 2, an electrically conductive via 14 in electrical communication with the silver layer 3 and the contact pad 12, and a porous membrane layer 8 overlaying the cavity 5 and defining a chamber 10 formed by the porous membrane layer 8, the walled cavity 5, and the cavity floor 4. In this embodiment, the via 14 communicably extends from the silver layer 3 through the substrate 2 to the contact pad 12 positioned on an outer surface of the substrate 2.

Figure 4:
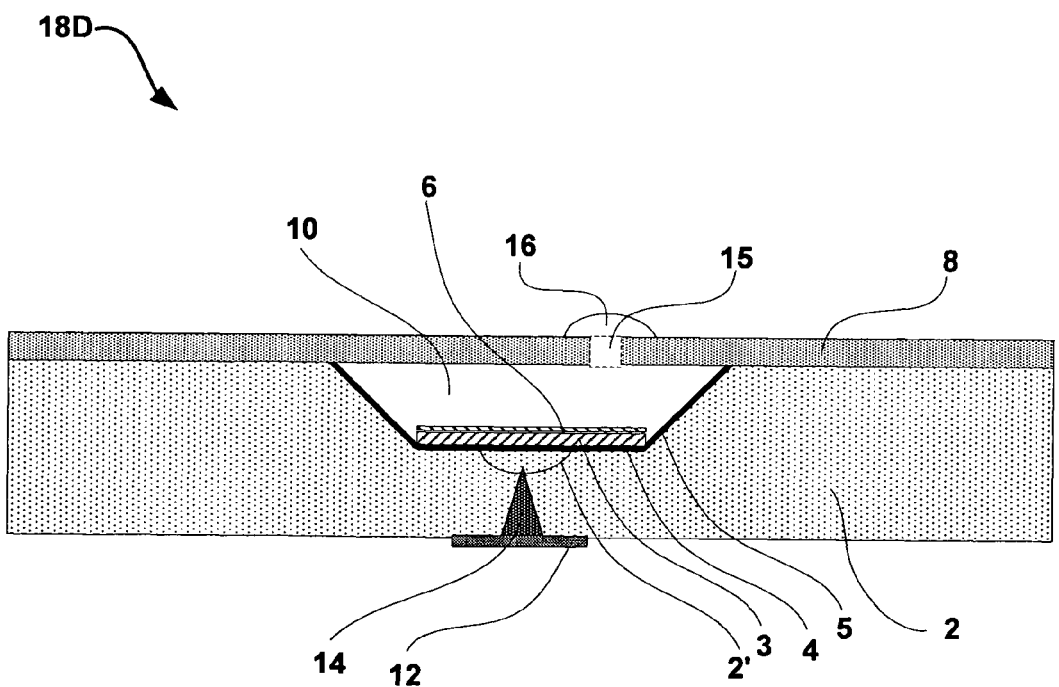
FIG. 4 is a cross-sectional side view diagram illustrating a reference electrode according to an embodiment of the invention.

In a variation of the embodiment of FIG. 3 illustrated in FIG. 4, the invention provides an electrode 18D including a substrate 2 defining a floor 4 of a walled cavity 5, a silver layer 3 overlaying at least a portion of the cavity floor 4, a silver chloride layer 6 overlaying at least a portion of the silver layer 3, an electrically conductive contact pad 12 positioned on an outer surface of the substrate 2 and overlaying at least a portion of the substrate 2, an electrically conductive via 14 in electrical communication with the silver layer 3 and the contact pad 12 through an ion doped conductive region 2' of the substrate 2, and a porous membrane layer 8 overlaying the cavity 5 and defining a chamber 10 formed by the porous membrane layer 8, the walled cavity 5, and the cavity floor 4. In this embodiment, the via 14 communicably extends from to the silver layer 3 through the ion doped conductive region 2' of the substrate 2, and extends through the substrate 2 to the contact pad 12 positioned on an outer surface of the substrate 2.

Figure 5:
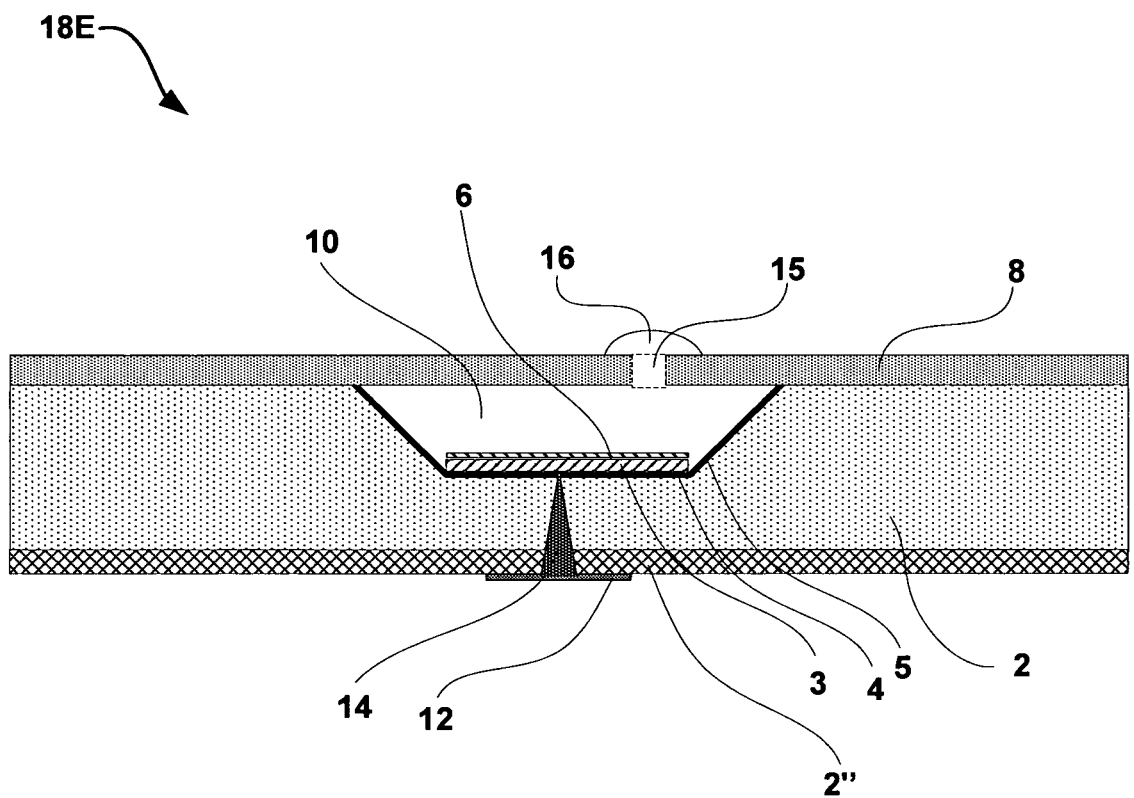
FIG. 5 is a cross-sectional side view diagram illustrating a reference electrode according to another embodiment of the invention.

In yet another embodiment illustrated in FIG. 5, the invention provides an electrode 18E including a substrate 2 formed on an insulative base 2", the substrate 2 defining a floor 4 of a walled cavity 5, a silver layer 3 overlaying at least a portion of the cavity floor 4, a silver chloride layer 6 overlaying at least a portion of the silver layer 3, an electrically conductive contact pad 12 positioned on an outer surface of the substrate 2 and overlaying at least a portion of the substrate 2, an electrically conductive via 14 connecting to the silver layer 3 and to the contact pad 12, and a porous membrane layer 8 overlaying the cavity 5 and defining a chamber 10 formed by the porous membrane layer 8, the walled cavity 5, and the cavity floor 4. In this embodiment, the via 14 communicably extends from the silver layer 3 through the substrate 2 and insulative base 2" to the contact pad 12.

In any or all of the embodiments illustrated in FIGS. 1-5, an optional electrolyte fill opening 15, which communicably extends to the chamber 10 through the top and bottom surface of the porous membrane layer 8, may be included. The electrolyte fill opening 15 can be used to add a liquid electrolyte to the chamber 10 after bonding together the porous membrane layer 8 and the walled cavity 5 to provide a hermetic seal for the chamber 10 where the cavity walls meet the inner surface of the porous membrane layer 8. An optional sealant bead 16 can be applied to the top surface of the porous membrane layer 8 to hermetically seal the electrolyte fill opening 15 and the chamber 10 after adding electrolyte to the chamber 10. The electrolyte may remain in a liquid state or may form a gel.

The substrate 2 of the electrode 18 may be made of an insulative material such as a ceramic material, but is preferably a semi-conductive material such as silicon. The ceramic material may be, for example, aluminum oxide or silicon dioxide or a combination thereof. In certain presently preferred embodiments, the substrate 2 is a semi-conductor such as silicon deposited on an insulator (i.e. a silicon on insulator substrate) or a glass (i.e. a silicon on glass substrate).

A conductive layer may be deposited overlaying the substrate 2 to form the walls of the walled cavity 5, wherein the floor 4 of the cavity 5 is formed by the substrate 2. An illustrative embodiment is shown in FIG. 1. In an alternative embodiment, an insulative layer 17 (FIG. 2) may be deposited on the substrate 2 in a pattern to form the walls of the walled cavity 5, wherein the floor 4 of the cavity 5 is formed by the substrate 2. An illustrative embodiment is shown in FIG. 2. In some embodiments, the cavity may have dimensions of about 1-20 mm in length, more preferably about 1-10 mm in width, and more preferably about 100-500 micrometers in depth. The depth will depend on the thickness of the silicon used to make the cavity.

The cathode layer, for example the Ag layer 3, may be deposited onto the substrate 2 by, e.g., electroplating, screen printing or vapor deposition, according to methods known in the art. The Ag layer 3 may be deposited on at least a portion of the floor 4 of a walled cavity 5, but may optionally be applied to at least a portion of the cavity walls. For electroplating of the Ag layer 3, a plating solution containing a soluble silver salt, for example silver nitrate, can be plated, for example by electroless plating, to the cavity floor and optionally to the walls of the cavity. For screen printing, the Ag particles may be combined with ceramic binding material in a liquid carrier and then screen printed, followed by drying to remove a portion of the liquid carrier and firing at high temperature (e.g., 700-800° C. For vapor deposition, Ag metal may be evaporated and condensed onto the support substrate 2 under high vacuum, for example.

In one embodiment according to the invention, an AgCl layer 6 is formed by electrodeposition of the Ag layer 3 with a chloride electrolyte solution having a concentration of between about 0.01 M and 1.0 M and a pH of about pH 1 to about pH 7 at a current density of about 0.005 to about 50 mA/mm$^2$ for about 30 seconds to 20 minutes. Preferably, electrodeposition is performed with a chloride electrolyte solution having a current density of about 5-36 mA/mm$^2$ for about 4-6 minutes.

The electrically conductive contact pads may be fabricated using a number of electrically conductive materials, including metals and metal alloys. Preferably, the electrically conductive contact pads are fabricated using one or more metals or metal alloys including gold, silver, platinum, palladium, aluminum, copper, tin, and the like. In some embodiments, the electrically conductive contact pads are deposited on a surface of the substrate 2, on a surface of an insulative layer 2' overlaying the substrate 2, or on a surface of the porous membrane layer 8 overlaying the substrate 2. Suitable methods of depositing the electrically conductive contact pads may be selected from one or more of evaporation, sputtering, electrodeposition, chemical vapor deposition, molecular beam epitaxy, and thermal oxidation. A preferred deposition method is electrodeposition.

The electrically conductive vias may also be fabricated using a number of electrically conductive materials, including metals and metal alloys. Preferably, the electrically conductive vias are fabricated using one or more metals or metal alloys including gold, silver, platinum, palladium, tin, and the like. In some embodiments, the electrically conductive vias are deposited on a surface of the substrate 2, on a surface of an insulative layer 2' overlaying the substrate 2, or on a surface of the porous membrane layer 8 overlaying the substrate 2. Suitable methods of depositing the via may be selected from one or more of evaporation, sputtering, electrodeposition, chemical vapor deposition, molecular beam epitaxy, and thermal oxidation. A preferred deposition method is sputtering.

The porous membrane layer 8 may be composed of silica or silicate glasses, and is preferably at least about 10 micrometers thick. The porous membrane layer 8 may alternatively be a flexible polymeric material that can transmit hydrogen ions (e.g. Nafion™ membrane available from DuPont Chemical Co., Wilmington Del.). The porous membrane layer 8 is preferably sized and shaped to cover any portion of the Ag layer 3 that is not covered with an AgCl layer 6 and may provide insulation of that portion of the Ag layer 3 that is not oxidized to form an AgCl layer 6 (e.g., around the edges of the Ag layer 3).

In one exemplary embodiment of preparing a monolithic electrode 18A illustrated in FIG. 1, a substrate 2, such as a silicon wafer, silicon on insulator, or silicon on glass substrate 2, may have an oxide and nitride layer grown on the surface, said layer to be masked in a pattern to define a cavity and the unmasked portion of the said layer partially etched away to define cavity walls 5, followed by bulk etching of the substrate 2 to create a cavity having a floor 4 and walls 5 defined by the substrate. The mask and said layer may then be removed and replaced with a mask covering the cavity but leaving exposed a portion of the substrate surface adjacent to the cavity walls 5. Aluminum may then be sputtered onto the surface of the substrate 2 to define an electrically conductive contact pad 12.

Next, a mask may be placed over the substrate 2 covering the surface except for the cavity floor 4 and cavity walls 5, and silver sputter deposited onto the substrate floor 4 and walls 5 of the cavity. The surface of the silver layer 3 may then be electrochemically chloridized using a sodium chloride electrolyte solution and a platinum electrode to form a silver chloride layer 6 at least partially overlaying the silver layer 3. Alternatively, at least a portion of the surface of the silver layer 3 may be chloridized by dipping the masked substrate into a molten salt bath containing silver chloride.

A porous membrane layer 8, for example, a porous glass plate preferably having a pre-etched hole positioned over the contact pad and an opening 15 extending from a top surface to a bottom surface of the glass plate, may then bonded to the surface of the substrate, for example, using anodic bonding, to define a chamber 10, with the opening 15 positioned over the floor of the cavity 4. The pre-etched hole may be filled with an electrically conductive material, for example, by electroless plating or sputter deposition of a metal through a mask positioned over the porous membrane layer 8 and having a mask opening positioned over the pre-etched hole in the porous membrane layer 8 to form a via 14 electrically connecting to the electrically conductive contact pad 12 and to the silver layer 4.

An electrolyte solution may then be added to the chamber 10 defined by the cavity floor 4, the cavity walls 5 and the porous membrane layer 8 through the pre-etched opening 15. This may be accomplished in any number of ways, for example, by inserting the tip of a syringe needle into the opening 15 and injecting the electrolyte, or by using the vacuum filling method described below, to draw the electrolyte through the opening 15 and into the chamber 10. The chamber 10 may then be sealed, for example, by applying a sealant bead 16 (e.g. a curable epoxy resin) positioned to occlude the opening 15.

Because injection of an electrolyte into the chamber 10 from a small diameter syringe needle may introduce microscopic gas bubbles into the electrolyte, a vacuum filling method of filling the chamber 10 with electrolyte may generally be preferred. In one exemplary vacuum filling method, the assembled monolithic electrode is placed in a vacuum chamber that is partially evacuated to create a vacuum. A volume of saturated electrolyte solution sufficient to fill the electrode chamber 10 is positioned over the opening 15 (e.g. as a droplet or liquid film), and the vacuum is subsequently released, drawing the electrolyte into the electrode chamber 10. Any excess electrolyte is removed from the surface of the porous membrane layer 8, and the chamber 10 is sealed, for example, by applying a sealant bead 16 (e.g. a curable epoxy resin) positioned to occlude the opening 15.

An alternative monolithic electrode fabrication and electrolyte filling method may be useful when a flexible polymeric material permeable to hydrogen ions is used as the porous membrane layer 8. The flexible polymeric material may be manufactured as a foil or film. An opening 15 may be created in the film (e.g. using laser cutting, mechanical punching, embossing or the like) and this film bonded to the substrate 2 with the opening 15 positioned over the chamber 15. Alternatively, the cavity may be filled with a sacrificial material, the polymeric material can be coated (e.g. spin coated as a solution) onto the surface of the substrate 2, an opening 15 can be created in the porous membrane layer 8, photo lithography can be used to create the cavity floor 4 and walls 5, and the chamber can then be created by etching the sacrifacial material.

In order to fill the chamber 10 with electrolyte, a hot electrolytic solution may be added to the chamber 10, or the chamber 10 may be filled with cold electrolyte and heated to an elevated temperature below the boiling point of the electrolyte. Next a force may be applied to the surface of the porous membrane layer 8 (e.g. by a "pick and place" type machine), forcing the excess electrolyte fluid to exit through the hole and building up a stress in the flexible porous membrane layer 8. At approximately the same time, a seal material may be pressed into the hole (e.g. using a similar "pick and place" machine). This seal material may be, for example, a small piece of the flexible polymer material making up the porous membrane layer 8, or a fast-setting liquid adhesive or sealant (e.g. a fast curing epoxy or isocyanate resin). Then the pressure on the cover may be released.

In another exemplary embodiment of preparing a monolithic electrode illustrated in FIG. 2, aluminum may be sputtered onto the surface of a substrate 2 such as a silicon wafer, silicon on insulator, or silicon on glass substrate, to define an electrically conductive contact pad 12. Next, a mask may be placed over the aluminum layer covering the contact pad 12, and at least a portion of the remaining aluminum etched away. The mask may then be removed and replace with a mask defining a cavity floor 4.

Silver may then be sputter deposited as a silver layer 3 onto the cavity floor 4 defined by the substrate 2 adjacent to and electrically connecting with the contact pad 12. At least a portion of the surface of the silver layer 3 may then be electrochemically chloridized to form a silver chloride layer 6 using, for example, a sodium chloride electrolyte solution and a platinum electrode. Alternatively, at least a portion of the surface of the silver layer 3 may be chloridized by dipping the substrate into a molten salt bath containing silver chloride.

The silver chloride layer 6, silver layer 3 and contact pad 12 may then be masked, and an insulative layer 17 formed over the substrate 2 surrounding the silver layer 3 to form cavity walls 5. This may be accomplished by etching to define cavity walls 5 and deep etching to form a cavity, followed by oxidation of a portion of any remaining aluminum layer to form an insulative layer 17 overlaying the substrate 2. Alternatively, another insulative layer (e.g. a ceramic material layer) may be deposited overlaying the substrate 2 to form cavity walls 5 surrounding the cavity floor 4 defined by the substrate 2 in the region left exposed by the mask.

The mask may then be removed and an opening etched from the surface of the insulative layer 17 through the insulative layer 17 down to the contact pad 12. An electrically conductive material, for example, a metal or metal alloy, may then be deposited (e.g. by evaporation or sputtering) into the etched opening to create an electrically conductive via 14 electrically connected to the silver cathode layer 3 through the contact pad 12.

A porous membrane layer 8, for example, a porous glass plate preferably having a pre-etched opening 15 extending from a top surface to a bottom surface of the glass plate, may then be bonded to the surface of the insulative layer 17 to define a chamber 10, for example, using anodic bonding, with the opening 15 positioned over the cavity floor 4. A hole may be drilled through the porous membrane layer 8 to the via 14, and the resulting hole filled with an electrically conductive material to complete formation of the via 14 so that the via 14 extends to the top surface of the porous membrane layer 8. This can be accomplished, for example, by electroless plating or sputter deposition of a metal through a mask positioned over the porous membrane layer 8, with the a mask opening positioned over the hole drilled in the porous membrane layer 8. This electrically conductive material becomes a surface electrical connect for the via 14, which electrically connects to the silver layer 3 through the contact pad 12.

An electrolyte solution may then be added to the chamber 10 defined by the cavity floor 4, the cavity walls 5 and the porous membrane layer 8 through the opening 15. This may be accomplished in any number of ways, for example, by inserting the tip of a syringe needle into the opening 15 and injecting the electrolyte into the chamber 10, or by using the previously described vacuum method to draw the electrolyte through the opening 15 and into the chamber 10. The chamber may then be sealed, for example, by applying a sealant bead 16 (e.g. a curable epoxy resin) positioned to occlude the opening 15.

In alternative exemplary embodiments of preparing a monolithic electrode illustrated in FIGS. 3 and 4, a cavity having a floor 4 and walls 5 defined by a substrate 2, such as a silicon wafer, silicon on insulator, or silicon on glass substrate, may be bulk etched into the top surface of the substrate 2. Optionally (as shown in FIG. 4), at least a portion of the floor 4 of the cavity may be heavily doped with conductive cationic species to form a conductive substrate region 2'.

Next, the bottom surface of the substrate may be deep etched through a mask to define an opening extending from the bottom of the substrate to either the cavity floor 4 or optionally (as shown in FIG. 4), to the doped conductive substrate region 2' under the cavity floor 4. The opening may then be filled with a conductive material such as a metal by sputtering through a mask having a mask opening positioned over the opening to define an electrically conductive via 14 extending from the bottom surface of the substrate 2 to the cavity floor 4, or optionally (as shown in FIG. 4), to the doped conductive substrate region 2'.

Next, a metallization pattern may be created, e.g. by electroless plating or sputtering through a mask, to define an electrically conductive contact pad 12 overlaying the substrate 2 on the bottom surface of the substrate 2 in electrical contact with the electrically conductive via 14. A mask may then be applied covering the top surface of the substrate 2 except for the cavity floor 4 and walls 5. Silver may then be sputter deposited as a cathode silver layer 3 onto at least the floor 4 of the cavity (and optionally the cavity walls 5), in electrical connection with the via 14, or optionally (as shown in FIG. 4), to the doped conductive substrate region 2', and to the contact pad 12. At least a portion of the surface of the silver layer 3 may then be electrochemically chloridized, for example, using a sodium chloride electrolyte solution and a platinum electrode, to form an AgCl layer 6 overlaying the silver layer 3. Alternatively, at least a portion of the silver layer 3 may be chloridized to form the silver chloride layer 6 by dipping the masked substrate 2 into a molten salt bath containing silver chloride.

A porous membrane layer 8, for example, a porous glass plate preferably having a pre-etched opening 15 extending from a top surface to a bottom surface of the porous membrane layer 8, may then be bonded, for example, using anodic bonding, to the top surface of the substrate 2 to form a chamber 10, with the opening 15 positioned over the cavity floor 4. An electrolyte solution may then be added to the chamber 10 defined by the cavity floor 4, the cavity walls 5 and the porous membrane layer 8 through the opening 15. This may be accomplished in any number of ways, for example, by inserting the tip of a syringe needle into the opening 15 and injecting the electrolyte into the chamber 10, or by using the previously described vacuum method to draw the electrolyte through the opening 15 and into the chamber 10. The chamber 10 may then be sealed, for example, by applying a sealant bead 16 (e.g. a curable epoxy resin) to occlude the opening 15.

Figure 6:
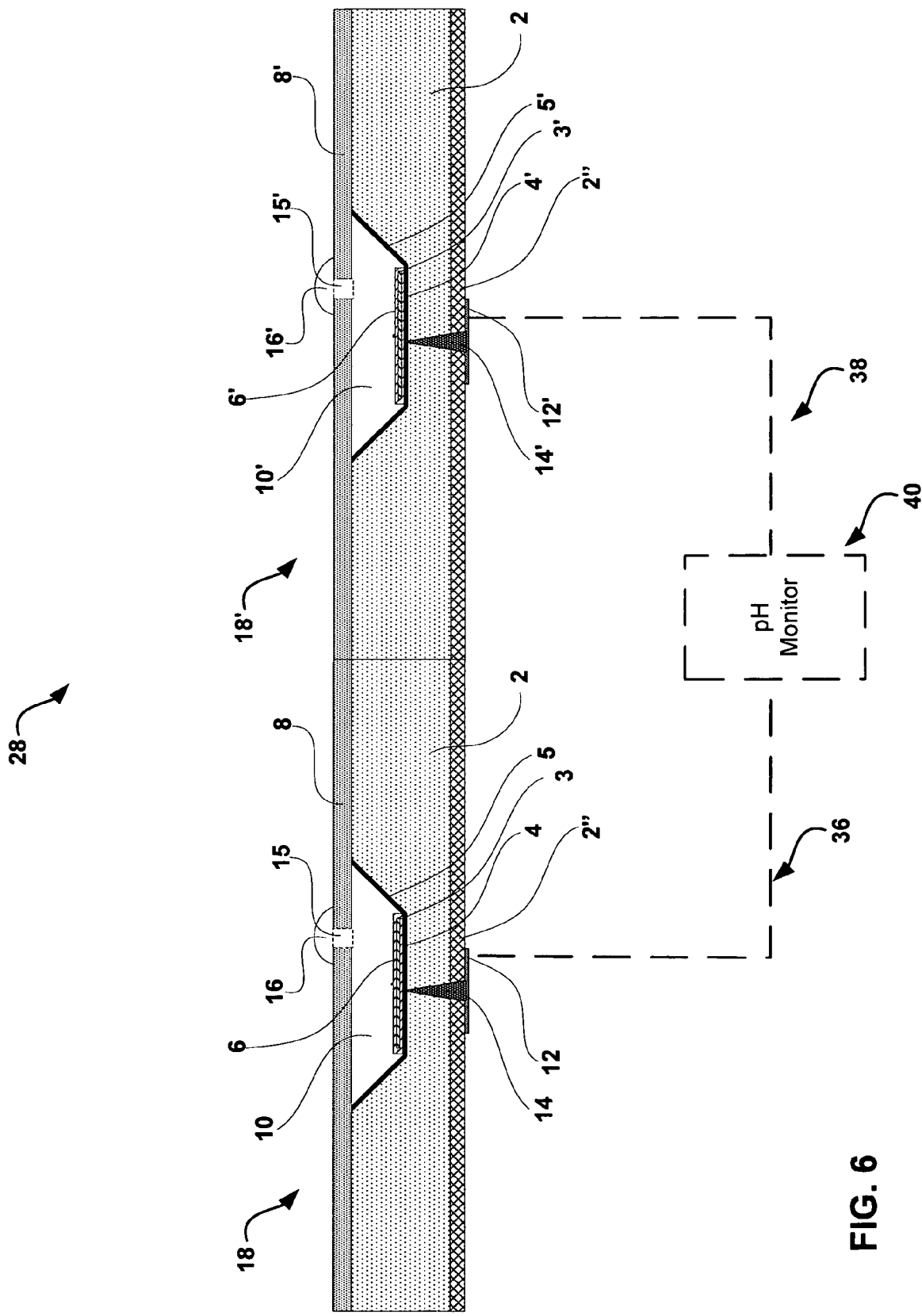
FIG. 6 is a cross-sectional side view diagram side view of one embodiment of a monolithic pH transducer incorporating an indicator electrode and a reference electrode.

In some embodiments illustrated in FIG. 6, the electrode may be used as a reference electrode 18. To operate as a reference electrode, an electrolyte solution may be added to the chamber 10 through the optional electrolyte fill opening 15, and then the opening 15 may be sealed with an optional sealant bead 16. Preferably, the electrolyte solution is selected to be an aqueous electrolyte solution, more preferably an aqueous electrolyte solution including one or more of hydrogen chloride, potassium chloride, silver chloride, and sodium chloride. For use as a reference electrode, the porous membrane layer 8 is preferably permeable to the electrolyte solution. More preferably, the porous membrane layer is permeable to hydrogen ions. The porous membrane layer 8 may be a glass plate, such as a porous glass plate, or a glass plate including a porous glass frit extending to the chamber 10 between the top surface and the bottom surface of the glass plate.

In other embodiments illustrated in FIG. 6, the electrode may be used as an indicator electrode 18'. To operate as an indicator electrode, an electrolyte solution may be added to the chamber 10 through the optional electrolyte fill opening 15, and then the opening 15 may be sealed with an optional sealant bead 16. Preferably, the electrolyte is selected to be an aqueous solution of one or more of hydrogen chloride, potassium chloride, and sodium chloride. For use as an indicator electrode, the porous membrane layer 8 may be selectively permeable to sodium ions and/or hydrogen ions. In some embodiments, the porous membrane layer 8 comprises sodium glass. Preferably, the porous membrane layer 8 comprises inner and outer hydrated gel layers surrounding a layer of dry sodium glass. More preferably, each of the hydrated gel layers has a thickness from about 5 to about 20 micrometers, and the layer of sodium glass has a thickness from about 50 to about 1000 micrometers, more preferably from about 100 to about 500 micrometers.

When used as a reference electrode, the electrolyte solution employed in the chamber 10 is selected to provide a liquid junction with a sample or a calibration solution and thereby isolates the indicator electrode from the varying electrochemical potentials of the calibrating solution or the sample to establish an environment in the reference electrode that is independent of the ionic activity of the sample or calibrating solution. The electrolyte solution for a reference electrode is preferably selected to be essentially a chloride solution (e.g., KCl) that is hypertonic relative to the sample or calibrating solutions.

In a preferred embodiment, the electrolyte solution is a 3.0 M KCl solution that is initially saturated with AgCl. The electrolyte solution may contain a surfactant at a concentration of between 0.01% and 1.0% by weight to reduce the likelihood of bubble formation when adding the electrolyte to the chamber 10. Suitable surfactants include polyoxyl hydrogenated castor oil 25 (e.g., Arlatone G™) and polyoxyethyleneglycol dodecyl ether (e.g. Brij 35™). In one embodiment, the electrolyte solution is prepared at room temperature and then saturated with excess AgCl. The saturated solution, containing suspended AgCl particles, may then be packaged in a sealed flexible container with no headspace. This technique may increase the likelihood that the electrolyte solution will remain saturated with AgCl at any storage temperature.

In another aspect, the invention provides a monolithic pH transducer including an indicator electrode electrically connected to a reference electrode. When the monolithic pH transducer is introduced to a fluid sample, the porous membrane layers of the indicator electrode 18' and the reference electrode 18 come into contact with the sample, forming a liquid junction between the electrolyte within the reference electrode chamber and the electrolyte within the indicator electrode chamber. The contact of sample with the electrolyte solution completes an electrical circuit from each of the reference electrode and the indicator electrode through electrical leads connected to a pH monitor 40 (FIG. 6).

FIG. 6 illustrates a monolithic pH transducer including a reference electrode 18 electrically connected to an indicator electrode 18' (hereinafter "pH transducer 28") by an external circuit through a pH monitor 40. This pH transducer 28 may also be referred to as a "probe," "capsule," or "pill". A pH transducer generally includes circuitry for providing an electrical signal whose electrical characteristics, such as current or voltage amplitude, frequency or pulse width, are proportional to the measured physiological parameter. This circuitry is shown schematically by the pH monitor 40 in FIG. 6. The detailed configuration of the pH monitor 40 is not critical to the present invention. However, the pH monitor 40 should generally incorporate circuitry suitable for high impedance measurement of an electrical current, an electrical voltage, or an electrical resistance. For example, the pH monitor may include an operational amplifier for amplifying the analog electrical signal from the pH sensing electrode, an analog to digital converter (ADC) for converting the analog signal to a digital signal, a microprocessor for processing the digital signal, and a telemetry unit for transmitting the processed digital signal to a recording device external to the body lumen.

In the particular embodiment illustrated in FIG. 6, pH is the physiological parameter to be sensed, and it is detected by a pH transducer 28 including a reference electrode 18 electrically connected to a pH monitor 40 by a first electrical lead 36 in electrical communication with a first electrically conductive contact pad 12, and an indicator electrode 18' electrically connected to the pH monitor 40 by a second electrical lead 38 in electrical communication with a second electrically conductive contact pad 12'.

In some embodiments not illustrated by FIG. 6, one or both of the electrical leads connect directly to one of the vias 14 or 14' extending through the substrate 2 and/or an insulative substrate layer 2'''. For example, if first electrical lead 36 electrically connects to the first via 14, then second electrical lead 38 may connect to the second via 14'.

The pH monitor 40 measures the potential difference between the indicator electrode 18' and the reference electrode 18. This potential difference is proportional to the concentration of the analyte in the sample or calibrating solution. For pH measurement, this potential difference is proportional to the hydrogen ion concentration in the sample of calibrating solution.

According to some embodiments of the present invention, a pH transducer may include additional sensors for detecting one or more additional physiological parameters, for example, body temperature. Although a pH sensor has been described herein, those skilled in the art will appreciate that a sensor of any of a variety of other physiological parameters, such as pressure or temperature, can be incorporated in a pH transducer. In certain embodiments, temperature and/or pressure may be sensed and transduced together with pH, in order to adjust the pH readings and make them more accurate, or to supply additional data helpful in the analysis of the patient's condition.

In some embodiments, the pH transducer may contain, for example, additional electrochemical sensors (i.e., electrodes) for measuring, e.g., $pCO_2$, $pO_2$, $Na+$, $Ca.++$, and hematocrit, together with the reference electrode 18. Alternatively, the pH transducer may contain enzyme sensors. Temperature sensing may be achieved by including a thermocouple, thermistor or equivalent temperature sensing device with the pH transducer.

In the example of FIG. 6, reference electrode 18 includes a substrate 2 having an insulative base 2'' the substrate 2 defining a first floor 4 of a first walled cavity 5, a first silver layer 3 overlaying at least a portion of the first cavity floor 4, a first silver chloride layer 6 overlaying at least a portion of the first silver layer 3, a first electrically conductive contact pad 12 positioned on an outer surface of the substrate 2 and overlaying at least a portion of the substrate 2, a first electrically conductive via 14 in electrical communication with the first silver layer 3 and the first contact pad 12, and a first porous membrane layer 8 overlaying the first cavity 5 and defining a first chamber 10 formed by the first porous membrane layer 8, the first walled cavity 5, and the first cavity floor 4. In this illustrative embodiment, the first via 14 extends through the substrate 2 and the insulative base 2'' to communicably connect the first silver layer 3 to the first contact pad 12.

Indicator electrode 18' includes the substrate 2 formed on the insulative base 2'' the substrate 2 defining a second floor 4' of a second walled cavity 5', a second silver layer 3' overlaying at least a portion of the second cavity floor 4', a second silver chloride layer 6' overlaying at least a portion of the second silver layer 3', a second electrically conductive contact pad 12' positioned on an outer surface of the substrate 2 and overlaying at least a portion of the substrate 2, a second electrically conductive via 14' in electrical communication with the second silver layer 3' and the second contact pad 12'; and a second porous membrane layer 8' overlaying the second cavity 5' and defining a second chamber 10' formed by the second porous membrane layer 8', the second walled cavity 5', and the second cavity floor 4'. In this illustrative embodiment, the second via 14' extends through the substrate 2 and the insulative base 2" to communicably connect the second silver layer 3' to the second contact pad 12'.

Generally, the first porous membrane layer 8 for the reference electrode 18 will be selected to be a different material from porous membrane layer 8' for the indicator electrode 18'. Preferably, the reference porous membrane layer 8 may be an electrolyte permeable polymer or porous glass, but generally is not a sodium glass. Preferably, the indicator electrode porous membrane layer 8' may be a sodium glass. In some embodiments not illustrated by FIG. 6, the substrate 2 may be formed from two separate wafers (e.g. n-type doped silicon) that are joined by an intervening insulative bonding layer to form the pH transducer 28.

As illustrated in FIG. 6, the reference electrode 18 and/or indicator electrode 18' may include optional electrolyte fill openings 15 and 15', respectively, which respectively communicably extend to the first chamber 10 and second chamber 10' through the top and bottom surfaces of the first porous membrane layer 8 and second porous membrane layer 8'. A liquid electrolyte may be added to the first chamber 10 and second chamber 10' after bonding one or both of the first and second porous membrane layers 8, 8'. Optional sealant beads 16 and 16' may be applied to occlude the first 15 and second 15' electrolyte fill openings after adding an electrolyte to the first 10 and second 10' chambers.

An electrode sensor including an indicator electrode and a reference electrode may need to be calibrated prior to determining the concentration of an analyte in a sample. The reference electrode 18 and indicator electrode 18' combination may be calibrated with at least one aqueous solution having a known value for the parameters to be measured by the electrode pair. Two calibrating solutions having different known values for a particular analyte allows the system to be calibrated on a 2-point basis, thereby improving the accuracy of the measurement of the range of analyte concentrations between the concentrations of the two calibrating solutions.

In one embodiment, a calibrating solution may be used to provide a baseline reading for the assembly combining reference electrode 18 and indicator electrode 18'. In another embodiment, the electrode sensor including an indicator electrode 18' and a reference electrode 18 may be calibrated with two calibrating solutions, e.g., calibrating solution A and calibrating solution B. The compositions of the two calibrating solutions may preferably be chosen so that for each of the characteristics measured by the system, a pair of values are obtained that are spaced over the range of permissible values that are measured by the electrode pair, providing a balanced 2-point calibration for the assembly 24.

Calibrating solutions of known standard pH are known to those skilled in the art as pH buffer solutions, and are generally based on U.S. National Bureau of Standards certified pH buffer solutions. Buffer solutions are sold commercially, for example, by Beckman Instruments, Inc., Irvine, Calif.

The invention may also provide a method and system for monitoring physiological parameters within a body lumen (cavity) using a sensing electrode transducer including a reference electrode according to an embodiment of the invention. The invention also includes methods for attaching a sensing electrode transducer to a wall of a body lumen. The term "lumen" as used herein refers to the space within a tubular wall (e.g., a vessel) or the cavity within a hollow organ. While the invention is described in detail as applied to the human esophagus, those skilled in the art will appreciate that it can apply to other body lumens or cavities, such as those of the stomach, colon, rectum, bladder, uterus, vagina, biliary ducts (including the common bile duct), or blood vessels. The term "esophagus" in this discussion includes the lower esophageal sphincter (LES). Where different embodiments have like elements, like reference numbers are used.

Figure 7:
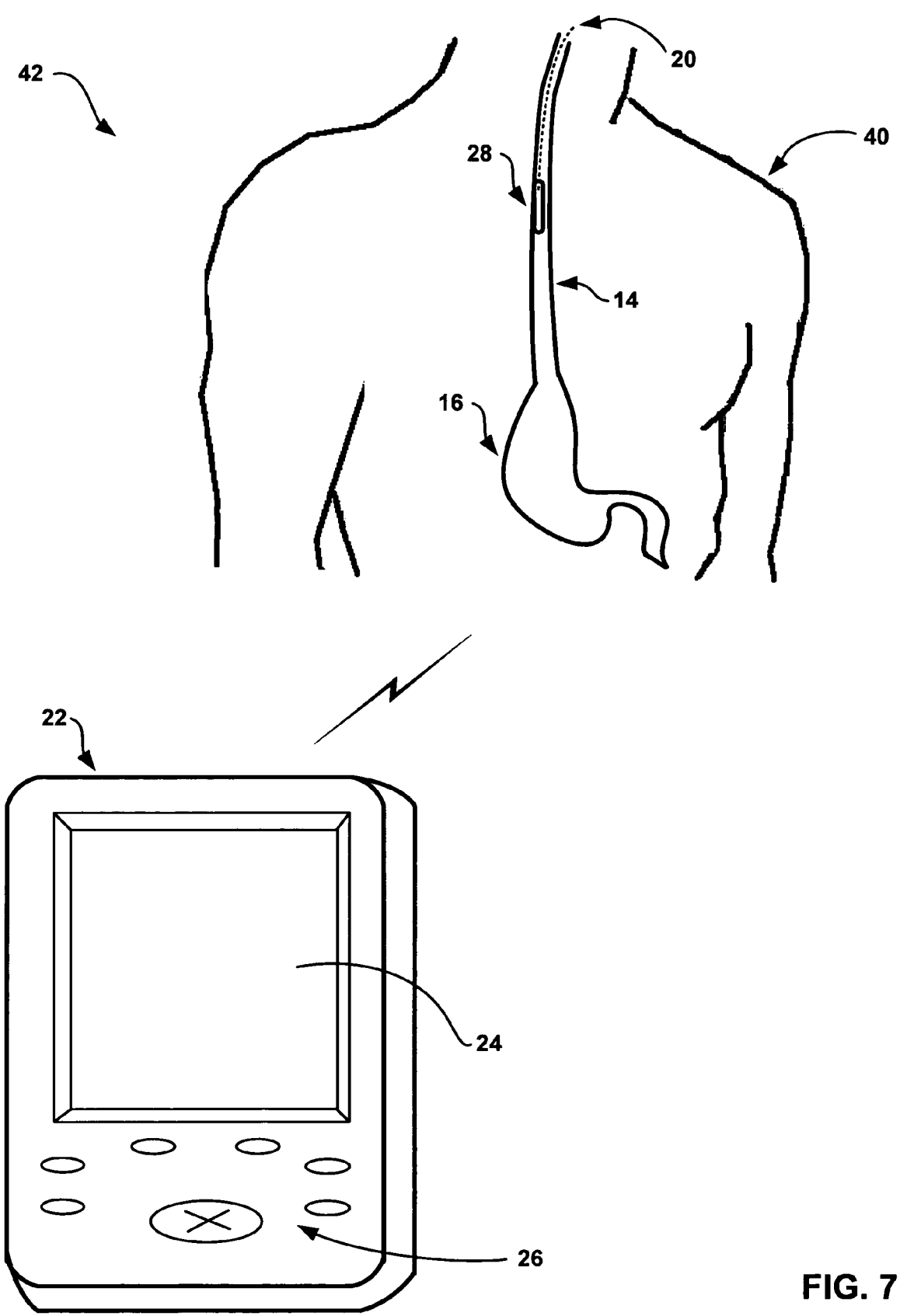
FIG. 7 is a schematic side view diagram of a human body having a monolithic pH transducer inserted within the esophagus.

FIG. 7 illustrates how physiological parameter data can be relayed by the pH transducer 28, which is positioned within the esophagus 14, to a radio frequency (RF) receiver 22 (hereinafter "radioreceiver") located outside the body of a person 40. As is illustrated in FIG. 6, more than one electrode 18 can be implanted so that data can be obtained from a plurality of different locations as will be described in greater detail below.

In certain embodiments, this transmission of data is accomplished via radio telemetry in real time. The RF receiver 22 receives physiological parameter data within about 12 seconds after the data are measured by the pH transducer 28. After reception of this data, the RF receiver 22 can be used to record, manipulate, process, interpret and/or display the data, using technology well known to those skilled in the art. In certain embodiments, the RF receiver 22 includes a display 24 for displaying data and a user interface 26 for controlling and/or programming the RF receiver 22. In certain embodiments, the patient can wear the receiver 22 and recorder on, for example, a belt, bracelet, arm or leg band, or necklace during the period of pH study or other analysis.

The receiver 22 and recording apparatus can have buttons or other switches thereon that enable the patient or other person to mark certain events in time during the recording period, such as when symptoms occur, when the patient is eating, when the patient is recumbent (either supine or prone), or when the patient is about to sleep. This event marking can be made in any recording medium that is used for recording the physiological parameter, such as magnetic tape or an electronic digital memory chip, in ways that are well known to those of skill in the art.

The pH transducer 28 can be made to sense the position of the patient, whether horizontal, vertical, or somewhere between horizontal and vertical. Such position sensing can be accomplished through the use of electrical switches that utilize floating fluid bubbles, as used in mechanical level sensing, electronic gyroscopic techniques, or MEMS accelerometers such as the VTI-Hamlin 3-axis accelerometer (available from VTI-Hamlin, Helsinki, Finland), as are known to those skilled in the art.

In certain embodiments, the pH transducer 28 can record and compress physiological parameter data as it is gathered, rather than transmit the data in real time. Following the assessment period, or at intervals therein, an external transceiver can be used to download pulses of condensed data. Transmission of data can be initiated at predetermined intervals or by an activation signal sent from the external transceiver or other activating device to the pH transducer 28, as will be understood by those of skill in the art. In this manner, a tabletop transceiver can be utilized, either at the patient's home, or in the physician's office or other clinical site.

In other embodiments, the pH transducer 28 can record, compress, and store physiological parameter data as it is gathered, using a memory chip and microprocessor. The person 40 can excrete the pH transducer 28 in his or her stool, and the pH transducer 28 can be retrieved. Subsequently, data stored in the pH transducer 28 can be downloaded into an external data retrieval device, which can be a computer or other analysis machine located outside the patient's body. This downloading can be accomplished by IR or RF transmission in response to an activation signal, using magnetic field or radiofrequency technology well known to those skilled in the art.

Although the typical gastroesophageal reflux study lasts 24 hours, other time periods for this study can exist, such as 48 hours or longer. Through the use of this invention, it is possible that fewer than 24 hours may be needed to establish the diagnosis of GERD, particularly because real-time monitoring can provide nearly immediate evidence of reflux events. The actual durations of various reflux studies using the present invention will be apparent to those of skill in the art.

The pH transducer 28 of FIG. 7 may also include an RF transmitter circuit and a power source. The RF transmitter circuit can comprise an antenna (or antenna coil), and the antenna can be at least in part external to the transducer housing. Alternatively, the antenna, if present, can be entirely self-contained within the pH transducer 28 housing. As an alternative to RF transmission, a signal that is indicative of the monitored parameter can be propagated through the patient's tissue from an electrical contact on the probe to a conductive dermal electrode or other conductor in contact with the patient.

When located within the electrode transducer housing, the power source can be a battery or capacitor or any other device that is capable of storing an electrical charge at least temporarily. In a battery powered embodiment, battery life can be extended by disconnecting the battery from other circuit components thereby limiting parasitic current drain. This can be accomplished in a variety of ways, such as by including a magnetically activated switch in the pH transducer 28. This switch can be used to connect or disconnect the battery as needed. By packaging the pH transducer 28 with an adjacent permanent magnet, the switch can be opened thereby disconnecting the battery and the shelf life of the device can thus be extended. Removing the pH transducer 28 from the packaging (and the adjacent permanent magnet) closes the switch and causes the battery to become connected and supply power to the pH transducer 28.

In alternative embodiments, the source of power to the pH transducer 28 can be external to the pH transducer 28 itself. For example, the pH transducer 28 can derive power from an external electromagnetic RF source, as occurs with passive RF telemetry techniques, such as RF coupling, that are well known to those skilled in the art. The pH transducer 28 can be energized by a time-varying RF wave that is transmitted by an external transceiver 32, also known as an "interrogator," which can also serve as a reader of data from the pH transducer 28. When the RF field passes through an antenna coil located within the pH transducer 28, an AC voltage is induced across the coil. This voltage is rectified to supply power to the pH transducer 28. The physiological parameter data stored in the pH transducer 28 can be transmitted back to an interrogator in a process often referred to as "backscattering." By detecting the backscattering signal, the data stored in the pH transducer 28 can be fully transferred.

Other possible sources of power for the pH transducer 28 include light, body heat, and the potential difference in voltage that can be generated in body fluids and detected by electrodes made of varying materials. The harnessing of such power sources for biotelemetry purposes is well described in R. Stuart Mackay: Bio-Medical Telemetry, Sensing and Transmitting Biological Information from Animals and Man, 2d ed., IEEE Press New York, 1993, whose section entitled "Electronics: Power Sources" is hereby incorporated herein by reference.

In alternative embodiments, a microprocessor, also called a central processing unit (CPU) may be used with the sensing pH transducer 28. This microprocessor can perform one or more functions, including temporary storage or memory of data, reception of input signal from the transducer, and transformation between analog and digital signals, among other functions that will be apparent to those skilled in the art.

Many other circuitry components that can help to generate, amplify, modify, or clarify the electrical signal can be used in other embodiments of the monitor. Such components include buffers, amplifiers, signal offset controls, signal gain controls, low pass filters, output voltage clamps, and analog-to-digital converters, among others. Numerous possible circuitry features of a portable pH monitoring device, all of which can be used in the present invention, are well described in U.S. Pat. No. 4,748,562 by Miller, et al., the disclosure of which is incorporated in its entirety herein by reference.

In certain embodiments, the pH transducer 28 further comprises a digital recorder or memory chip (not illustrated), which records the transduced physiological parameter data. This recorder or memory chip will allow temporary storage of this data accumulated over time (e.g., over a period of 24 hours for a typical gastroesophageal reflux study).

In certain embodiments, the pH transducer 28 includes a housing which surrounds the substrate 2 and which facilitates exposure of the porous membrane layer 8 to an external environment, for example, a liquid environment, without exposing the pH monitor 40 or other electrical components to that environment. In one presently preferred embodiment, a housing surrounds the electrical components of the pH transducer 28, thereby offering protection to those components from exposure to harmful or corrosive body fluids, environmental exposure, shock, and like factors which could damage or degrade the performance of these electrical components. The pH transducer 28 may be recessed within the housing and exposed to the external environment through a fluid port. Alternatively, the electrode transducer 18 may be mounted in a wall of the housing, or positioned on the exterior surface of the housing, depending upon the nature of the pH transducer 28 and its fluid contact and surface area requirements.

The transducer is preferably in electrical communication with a pH monitor, a transmitter, a microprocessor (CPU) and a power supply as previously described. Preferably, one or more of the pH monitor, the optional radiofrequency transmitter, the optional power supply, and the optional microprocessor are encased within the housing.

The housing can be made of any of various materials, including plastics such as polycarbonates, polyethylene, polytetrafluoroethelyne (Teflon™), nylon, polyoxymethylene (Delrin™), or polyethylene terephthalate (PET). The material used for the housing 120 should be resistant to water and acidic environments because the housing will be exposed, in some embodiments, to food, water, and gastrointestinal contents, including gastric acid, which is very caustic (with a pH of approximately 1).

The housing can have a lubricious coating applied to its outer surface, which reduces friction between the housing and any object or material that comes in contact with the housing, such as the esophageal wall or any food or fluids that flow down the esophagus 14 past the monitor. Such a coating can be made of silicone, silicone derivatives, or other hydrophilic materials that will be apparent to those skilled in the art. This slippery coating on the surface of the housing may reduce the likelihood of occurrence of the following events: (1) ingested material adhering to the pH transducer 28, (2) the esophagus 14 will become irritated from repeated contact with the pH transducer 28 during peristalsis of the esophagus 14, and (3) peristalsis or flowing food or fluid causing detachment of the pH transducer 28 from its attachment site.

The housing preferably has a shape with dimensions sufficiently small to permit insertion of the transducer into a human esophagus. In some embodiments, the shape of the housing is streamlined with smooth rounded corners. In certain embodiments, the shape of the housing can resemble that of a pill or gel capsule, as commonly used in various oral drug delivery systems. This feature helps to avoid injury to the gastrointestinal mucosa during endoscopic placement of the pH transducer 28, while the pH transducer 28 is attached to the esophagus, and, when the pH transducer 28 becomes detached from the esophageal wall, while the pH transducer 28 passes through the gastrointestinal tract and is excreted in the stool. Preferably, detachment occurs from about 2 days to about 10 days following attachment to the esophageal wall.

The pH transducer 28 can be placed in the esophagus 14 in a variety of ways. In certain embodiments of the present method, the pH transducer 28 is placed into the esophagus 14 through the use of a flexible or rigid endoscope 160 inserted through the nose or mouth of the person 40. The pH transducer 28 can be constrained within or by a deployment device, such as a catheter 20, until the physician visually verifies attachment through the endoscope. Then the pH transducer 28 can be intentionally deployed and left within the esophagus, using methods known to those of skill in the art. In other embodiments, a physician can attach the pH transducer 28 directly to the inner aspect of the esophageal wall through an opening in the esophagus 14 (esophagotomy) or stomach 16 (gastrotomy).

The physiological pH transducer 28 can be attached to the esophagus 14 in a variety of ways, also referred to herein as "attachment means." In accordance with a further aspect of the present invention, the monitoring device may be provided with a tissue attachment device. Suitable transducer placement and tissue attachment devices are described in U.S. Pat. No. 6,689,056 by Kilcoyne et al., the disclosure of which is incorporated herein in its entirety by reference.

The invention may be embodied in other specific forms without departing form the spirit or essential characteristics thereof. The foregoing embodiments are therefore to be considered in all respects illustrative rather than limiting on the invention described herein. The scope of the invention is thus encompassed by the claims rather than by the foregoing description, and all embodiments, variations and modifications that come within the meaning and range of equivalency of the claims are intended to fall within the scope of the invention. Various embodiments of the invention have been described. These and other embodiments are within the scope of the following claims.

The invention claimed is:

1. An electrode comprising:
   a single substrate defining a floor and walls of a walled cavity;
   an electrically conductive cathode layer overlaying at least a portion of the floor of the walled cavity;
   an electrically conductive contact pad overlaying at least a portion of the single substrate;
   an electrically conductive via in electrical communication with the cathode layer and the contact pad; and
   a porous membrane layer overlaying the cavity, wherein the porous membrane layer, the walls of the walled cavity, and the floor of the walled cavity define a chamber.

2. The electrode of claim 1, wherein the cathode layer comprises one or more metals selected from the group consisting of silver, gold, platinum, palladium, rhenium and mercury.

3. The electrode of claim 1, wherein the cathode layer comprises a silver chloride layer overlaying a silver layer.

4. The electrode of claim 1, further comprising an electrolyte within the chamber.

5. The electrode of claim 4, wherein the electrolyte is selected from the group consisting of aqueous solutions of one or more of hydrogen chloride, potassium chloride, silver chloride, and sodium chloride.

6. The electrode of claim 1, wherein the walls of the walled cavity and the porous membrane layer are bonded together to provide a seal for the chamber.

7. The electrode of claim 1, wherein the contact pad is positioned on a surface of the single substrate.

8. The electrode of claim 1, wherein the contact pad is positioned on a surface of the porous membrane layer.

9. The electrode of claim 1, wherein the single substrate is selected from the group consisting of silicon, silicon on glass, and silicon on insulator.

10. The electrode of claim 1, wherein the porous membrane layer comprises a glass plate or a polymer.

11. The electrode of claim 10, wherein the porous membrane layer further comprises a glass frit extending between a top surface and a bottom surface of the glass plate.

12. The electrode of claim 10, wherein the porous membrane layer further defines an opening communicably extending to the chamber between a top surface and a bottom surface of the glass plate.

13. The electrode of claim 12, wherein the opening is sealed with a sealant bead positioned to occlude the opening.

14. The electrode of claim 1, wherein the electrode is a reference electrode and the porous membrane layer is permeable to an electrolyte within the chamber.

15. The electrode of claim 1, wherein the electrode is an indicator electrode and the porous membrane layer is selectively permeable to at least one of sodium ions and hydrogen ions.

16. A pH transducer comprising:
    a single substrate;
    a pH indicator electrode formed on the single substrate; and
    a pH reference electrode formed on the single substrate and electrically connected to the indicator electrode by way of circuitry, wherein at least one of the pH indicator electrode or the pH reference electrode is defined by:
       a walled cavity having a floor and walls defined by the single substrate;
       an electrically conductive cathode layer overlaying at least a portion of the floor of the walled cavity;
       an electrically conductive contact pad overlaying at least a portion of the single substrate;
       an electrically conductive via in electrical communication with the cathode layer and the contact pad;
       a porous membrane layer overlaying the cavity, and wherein the porous membrane layer, the walls of the walled cavity, and the floor of the walled cavity define a chamber.

17. The pH transducer of claim 16, wherein the single substrate comprises silicon.

18. The pH transducer of claim 16, wherein the pH indicator electrode is defined by:
    a first walled cavity having a first floor and first walls defined by the single substrate;

a first silver layer overlaying at least a portion of the first cavity floor;

a first silver chloride layer overlaying at least a portion of the first silver layer;

a first electrically conductive contact pad overlaying at least a portion of the single substrate;

a first electrically conductive via in electrical communication with the first silver layer and the first contact pad; and a first porous membrane layer overlaying the first cavity, wherein the first porous membrane layer, the first walls, and the first cavity floor define a first chamber.

19. The pH transducer of claim 18, wherein the reference pH electrode is defined by:

a second walled cavity having a second floor and second walls defined by the single substrate;

a second silver layer overlaying at least a portion of the second cavity floor;

a second silver chloride layer overlaying at least a portion of the second silver layer;

a second electrically conductive contact pad overlaying at least a portion of the single substrate;

a second electrically conductive via in electrical communication with the second silver layer and the second contact pad; and a second porous membrane layer overlaying the second cavity, wherein the second porous membrane layer, the second walls, and the second cavity floor define a second chamber.

20. The pH transducer of claim 19, further comprising a first electrolyte within the first chamber, and a second electrolyte within the second chamber.

21. The pH transducer of claim 20, wherein the second porous membrane layer is permeable to the electrolyte within the second chamber.

22. The pH transducer of claim 19, wherein the first and second electrolytes are compositionally different.

23. The pH transducer of claim 19, wherein the first and second electrolytes are selected from the group consisting of aqueous mixtures of one or more of hydrogen chloride, potassium chloride, silver chloride, and sodium chloride.

24. The pH transducer of claim 19, wherein one or both of the first and second contact pads is positioned on a surface of the single substrate.

25. The pH transducer of claim 19, wherein the first contact pad is positioned on a surface of the first porous membrane layer, and the second contact pad is positioned on a surface of the second porous membrane layer.

26. The pH transducer of claim 19, wherein the first and second porous membrane layers comprise an integral glass sheet overlaying and bonded to each of the first and second walled cavities to provide a hermetic seal for the first and second chambers.

27. The pH transducer of claim 19, wherein the second porous membrane layer is permeable to an aqueous electrolyte.

28. The pH transducer of claim 19, wherein the second porous membrane layer further comprises a glass frit extending between a top surface and a bottom surface of the second porous membrane layer.

29. The pH transducer of claim 19, wherein the first porous membrane layer further defines a first opening communicably extending from an outer surface of the first porous membrane layer to the first chamber, and the second porous membrane layer further defines a second opening communicably extending from an outer surface of the second porous membrane layer to the second chamber.

30. The pH transducer of claim 29, wherein the first opening is sealed with a first sealant bead, and the second opening is sealed with a second sealant bead.

31. The pH transducer of claim 18, wherein the first porous membrane layer comprises sodium glass.

32. The pH transducer of claim 31, wherein the first porous membrane layer comprises inner and outer hydrated gel layers surrounding a layer of dry sodium glass.

33. A method for fabricating a monolithic pH electrode, comprising:

forming a cavity in a surface of a single substrate, wherein the cavity has a floor and walls defined by the single substrate;

depositing a silver layer overlaying at least a portion of the cavity floor;

depositing a silver chloride layer overlaying at least a portion of the silver layer;

depositing an electrically conductive contact pad overlaying at least a portion of the single substrate;

forming an electrically conductive via in electrical communication with the silver layer and the contact pad; and applying a porous membrane layer overlaying the cavity to define a chamber formed by the porous membrane layer, the walls of the cavity, and the cavity floor.

34. The method of claim 33, further comprising forming a housing around the substrate to hold the substrate in a position that exposes an outer surface of the porous membrane layer.

35. The method of claim 33, further comprising forming an opening communicably extending to the chamber from an outer surface of the porous membrane layer to an inner surface of the porous membrane layer.

36. The method of claim 35, further comprising bonding the inner surface of the porous membrane layer to the walls of the cavity, adding an electrolyte to the chamber through the opening, and hermetically sealing the chamber.

37. A method for sensing pH within a body lumen, comprising:

inserting into a body lumen a monolithic pH transducer comprising a single substrate, a pH indicator electrode formed on the single substrate, a pH reference electrode formed on the single substrate and electrically connected to the indicator electrode through a high impedance pH monitor formed on the single substrate, wherein at least one of the pH indicator electrode or the pH reference electrode is defined by:

a walled cavity having a floor and walls defined by the single substrate;

an electrically conductive cathode layer overlaying at least a portion of the floor of the walled cavity;

an electrically conductive contact pad overlaying at least a portion of the single substrate;

an electrically conductive via in electrical communication with the cathode layer and the contact pad;

a porous membrane layer overlaying the cavity, and wherein the porous membrane layer, the walls of the walled cavity, and the floor of the walled cavity define a chamber;

attaching the pH transducer to an inner wall of the body lumen; and recording the pH within the body lumen as measured by the pH monitor and pH transducer.

38. The method of claim 37, wherein the body lumen is an esophagus, and the recorded pH is an intraesophageal pH.

39. The electrode of claim 1, wherein the electrically conductive via communicably extends through a top surface and a bottom surface of the porous membrane layer.

* * * * *